United States Patent
Fey et al.

(10) Patent No.: US 9,850,458 B2
(45) Date of Patent: Dec. 26, 2017

(54) BIOREACTOR WITH LID FOR EASY ACCESS TO INCUBATION CAVITY

(75) Inventors: Stephen John Fey, Blommenslyst (DK); Krzysztof Wrzesinski, Odense S (DK)

(73) Assignee: DRUGMODE APS, Hoersholm (DK)

( * ) Notice: Subject to any disclaimer, the term of this patent is extended or adjusted under 35 U.S.C. 154(b) by 809 days.

(21) Appl. No.: 13/990,198

(22) PCT Filed: Dec. 7, 2011

(86) PCT No.: PCT/DK2011/050466
§ 371 (c)(1),
(2), (4) Date: May 29, 2013

(87) PCT Pub. No.: WO2012/079577
PCT Pub. Date: Jun. 21, 2012

(65) Prior Publication Data
US 2013/0260450 A1    Oct. 3, 2013

Related U.S. Application Data

(60) Provisional application No. 61/423,145, filed on Dec. 15, 2010.

(30) Foreign Application Priority Data

Dec. 15, 2010    (DK) .................. 2010 01127

(51) Int. Cl.
*C12M 1/26* (2006.01)
*C12M 1/04* (2006.01)
(Continued)

(52) U.S. Cl.
CPC ............ *C12M 23/24* (2013.01); *C12M 23/38* (2013.01); *C12M 27/10* (2013.01); *C12M 33/14* (2013.01); *C12M 35/04* (2013.01)

(58) Field of Classification Search
CPC ...... C12M 23/24; C12M 23/38; C12M 27/10; C12M 33/14; C12M 35/04
(Continued)

(56) References Cited

U.S. PATENT DOCUMENTS

| 4,142,940 A | 3/1979 | Modolell et al. |
| 4,734,372 A | 3/1988 | Rotman |

(Continued)

FOREIGN PATENT DOCUMENTS

| JP | 2009-118820 | 6/2009 |
| JP | 2009-273399 | 11/2009 |

(Continued)

OTHER PUBLICATIONS

International Search Report from International Application No. PCT/DK2011/050466 dated Mar. 7, 2012.
(Continued)

*Primary Examiner* — Michael L Hobbs
*Assistant Examiner* — Liban M Hassan
(74) *Attorney, Agent, or Firm* — Merchant & Gould P.C.

(57) ABSTRACT

There is provided a bioreactor which is provided with a lid (13) that facilitates access to the incubation cavity. Specifically the end wall of the incubation cavity is constituted by the lid (13) so that removal of the cap renders the incubation cavity fully accessible.

10 Claims, 2 Drawing Sheets

Lid    Conduit    Reservoir

(51) Int. Cl.
  *C12M 1/00* (2006.01)
  *C12M 3/04* (2006.01)
  *C12M 1/42* (2006.01)

(58) Field of Classification Search
  USPC ......... 435/289.1, 297.1, 297.3, 303.1, 305.1, 435/818
  See application file for complete search history.

(56) References Cited

U.S. PATENT DOCUMENTS

| | | | |
|---|---|---|---|
| 4,839,292 A | 6/1989 | Cremonese | |
| 5,026,650 A | 6/1991 | Schwarz et al. | |
| 5,153,131 A | 10/1992 | Wolf et al. | |
| 5,288,638 A * | 2/1994 | Lemonnier | C12M 23/10 210/244 |
| 5,437,998 A | 8/1995 | Schwartz et al. | |
| 5,507,949 A | 4/1996 | Ho | |
| 5,576,211 A | 11/1996 | Falkenberg et al. | |
| 5,665,594 A | 9/1997 | Schwarz et al. | |
| 5,702,945 A | 12/1997 | Nagels et al. | |
| 5,935,845 A | 8/1999 | Koontz | |
| 5,989,913 A | 11/1999 | Anderson et al. | |
| 5,998,202 A | 12/1999 | Schwarz et al. | |
| 6,001,643 A * | 12/1999 | Spaulding | C12M 23/34 435/288.2 |
| 6,607,910 B1 | 8/2003 | Dimitrijevich et al. | |
| 6,642,019 B1 | 11/2003 | Anderson et al. | |
| 2004/0203140 A1 | 10/2004 | Akers et al. | |
| 2005/0084965 A1 | 4/2005 | Silber et al. | |
| 2005/0148068 A1 | 7/2005 | Lacey et al. | |
| 2007/0298451 A1 * | 12/2007 | Ribault | C12Q 1/24 435/30 |
| 2008/0009027 A1 * | 1/2008 | Fraker | C12M 23/04 435/29 |
| 2008/0293091 A1 * | 11/2008 | Kanipayor | C12M 23/12 435/29 |
| 2010/0120136 A1 | 5/2010 | Larsen et al. | |

FOREIGN PATENT DOCUMENTS

| | | |
|---|---|---|
| WO | WO 95/07344 | 3/1995 |
| WO | 97/16536 A1 | 5/1997 |
| WO | 2007/076865 A1 | 7/2007 |
| WO | WO 2008/073313 | 6/2008 |

OTHER PUBLICATIONS

International Search Report from International Application No. PCT/DK2011/050294, dated Nov. 14, 2011.

* cited by examiner

Lid    Conduit    Reservoir

BIOREACTOR WITH LID FOR EASY ACCESS TO INCUBATION CAVITY

This application is a National Stage Application of PCT/DK2011/050466, filed 7 Dec. 2011, which claims benefit of Serial No. PA 2010 01127, filed 15 Dec. 2010 in Denmark, and Ser. No. 61/423,145, filed 15 Dec. 2010 in the United States, and which applications are incorporated herein by reference. To the extent appropriate, a claim of priority is made to each of the above disclosed applications.

FIELD OF THE INVENTION

The present invention relates to a bioreactor which is provided with a lid that facilitates easy and rapid access to the incubation cavity. Specifically the end wall of the incubation cavity is constituted by the lid so that removal of this lid renders the incubation cavity fully accessible.

BACKGROUND OF THE INVENTION

During "classical" cell culture in an essentially flat culture vessel, primary cells in general and biopsies in particular tend to de-differentiate. Visibly, biopsies exhibit the 'melting ice-cream effect' as cells migrate from a block of tissue out onto the flat supporting surface of the culture vessel. Gene expression is altered in these "migrating" cells, which begin to behave biochemically as isolated cells rather than as cellular components of a differentiated tissue. De-differentiated cells express different biochemical pathways than those normally expressed by corresponding cells in an intact organism. In addition, immortal cells normally have lost some or many of their specialised functions compared to the corresponding mortal cell in the intact organism In contrast with "classical" cell culture conditions, "microgravity" conditions preserve the differentiation state of many types of cells in culture. Microgravity bioreactors maintain microgravity conditions by continuous rotation of a typically cylindrical or tubular incubation cavity or compartment. This rotation continuously helps to prevent cells from adhering to the walls of the incubation cavity, suspending the cells in a fluid environment using a minimum shear force. This induces them to interact and to aggregate into colonies. These colonies have been given a variety of names including spheroids, cell conglomerates, cell aggregates and ProtoTissue™ (all of which are considered equivalent herein). For microgravity culturing, cells are often initially sown out onto small (ca. 100 μm diameter) beads (this accelerates the formation of microtissue structures) but is not essential and there are several other alternatives published in the literature for example using scaffolds [Lee K W, Wang S, Dadsetan M, Yaszemski M J, Lu L. Enhanced cell ingrowth and proliferation through three dimensional nano composite scaffolds with controlled pore structures. Biomacromolecules. 11:682-9, 2010] or cross-linked hydrogels [Villanueva I, Klement B J, Von Deutsch D, Bryant S J. Cross-linking density alters early metabolic activities in chondrocytes encapsulated in poly(ethylene glycol) hydrogels and cultured in the rotating wall vessel. Biotechnol Bioeng. 102:1242-50, 2009]. As Spheroids are formed by cell growth around these beads, the beads usually become completely covered with cells. Spheroids formed in this manner become highly differentiated so as to resemble adult tissue [Navran S. The application of low shear modelled microgravity to 3-D cell biology and tissue engineering. Biotechnol Ann Rev. 14: 275-296, 2008] [Freed L E, Vunjak-Novakovic G and Langer R. Cultivation of Cell-Polymer Cartilage Implants in Bioreactors. J Cell Biochem. 51: 257-64, 1993][Brown L A, Arterburn L M, Miller A P, Cowger N L, Hartley S M, Andrews A, Silber P M, Li A P. Maintenance of Liver Functions in Rat Hepatocytes Cultured as Spheroids in a Rotating Wall Vessel. In Vitro Cell Dev Biol Anim.; 39: 13-20, 2003].

Microgravity bioreactors have been used in a variety of contexts. Early studies showed that microgravity bioreactor systems helped cells form three dimensional structures by reducing shear stress on the cells [Reduced shear stress: a major component in the ability of mammalian tissues to form three-dimensional assemblies in simulated microgravity. Goodwin T J, Prewett T L, Wolf D A, Spaulding G F. J Cell Biochem. 1993 March; 51(3):301-11].

Now a significant body of literature demonstrates increased differentiation of cells grown in a microgravity bioreactor system. For reviews see: [[Navran S. The application of low shear modelled microgravity to 3-D cell biology and tissue engineering. Biotechnol Ann Rev. 14: 275-296, 2008] and [Growing tissues in microgravity. Unsworth B R, Lelkes P I. Nat Med. 1998 Aug.; 4(8):901-7.] For example, microgravity culturing induces neural precursor cells to form cellular clusters or "neurospheres". These neurospheres are characterized by a crude, but organized, architecture, having a surface layer of immature proliferating cells (nestin- and proliferating cell nuclear antigen-positive) that enclose strata of more differentiated cells (beta-tubulin III- and glial fibrillary acidic protein-positive). These "neurospheres" show promise for development of neurotransplantable tissue. See e.g. [Neural precursor cells form rudimentary tissue-like structures in a rotating-wall vessel bioreactor. Low H P, Savarese™, Schwartz W J. In vitro Cell Dev Biol Anim. 2001 March; 37(3):141-7.] and see [Rapid differentiation of NT2 cells in Sertoli-NT2 cell tissue constructs grown in the rotating wall bioreactor. Saporta S, Willing A E, Shamekh R, Bickford P, Paredes D, Cameron D F. Brain Res Bull. 2004 December 150; 64(4): 347-56.].

Or for another example, microgravity culturing of a multipotential human retinal cell line induced expression of a nearly in vivo phenotype, which could not be achieved when the cells were grown under other conditions [Generation of 3D retina-like structures from a human retinal cell line in a NASA bioreactor. Dutt K, Harris-Hooker S, Ellerson D, Layne D, Kumar R, Hunt R. Cell Transplant. 2003; 12(7):717-31.] Improved differentiation has also been demonstrated in other tissues [Freed L E, Vunjak-Novakovic G and Langer R. Cultivation of Cell-Polymer Cartilage Implants in Bioreactors. J Cell Biochem. 51: 257-64, 1993] [Brown L A, Arterburn L M, Miller A P, Cowger N L, Hartley S M, Andrews A, Silber P M, Li A P. Maintenance of Liver Functions in Rat Hepatocytes Cultured as Spheroids in a Rotating Wall Vessel. In Vitro Cell Dev Biol Anim.; 39: 13-20, 2003]. Some technical problems with microgravity bioreactors have been reported. For example, when temporomandibular joint (TMJ) disc tissues were engineered using either flat culture or a microgravity bioreactor, there were no significant differences in total matrix content and compressive stiffness, notwithstanding marked differences in gross appearance, histological structure, and distribution of collagen types I and II (with the bioreactor discs having more collagen type II). The authors concluded that improvements of the microgravity bioreactor culture system were needed [Detamore M S, Athanasiou K A. Use of a rotating bioreactor toward tissue engineering the temporomandibular joint disc. Tissue Eng. 2005 Jul.-Aug.; 11(7-8):1188-97]. The DNA repair system also seems to be detrimentally influenced [Kumari R, Singh K P, Dumond J W Jr. Simulated microgravity decreases DNA repair capacity and induces DNA damage in human lymphocytes. J. Cell Biochem. 107:723-31, 2009]. Although well known and widely used, currently available microgravity bioreactors have significant limitations:

Another significant limitation of microgravity bioreactors of the prior art is moisture loss, which affects cell growth. Dehydration (even only by 5-10%) during incubation can result in changes in pH and other concentration-dependent parameters, such as concentrations of salts, nutrient substances, and the like. Many cell types are highly sensitive to their environment. For such cells, even a small change in such environmental conditions can influence cell growth and gene expression. This problem is especially pronounced in a small volume bioreactor, where small changes in volume can cause relatively large changes in concentration-dependent parameters. Without some solution to this dehydration problem, a small volume bioreactor would experience rapid loss of moisture, notwithstanding maintenance of humidified conditions (100% relative humidity) in the incubator where the bioreactor was used. This tendency for rapid dehydration in a small volume bioreactor, that is, this tendency for rapid change in relative volume greatly increases the need for time-consuming manual monitoring and manipulation, for example to replenish or exchange culture medium. This tendency effectively renders long-term maintenance of cultures in a small volume bioreactor impractical or impossible. Accordingly, it would be advantageous to provide a microgravity bioreactor with very high relative water retention in the cell incubation compartment.

Still another limitation of microgravity bioreactors of the prior art is that access ports used for adding or removing cells and growth medium have typically relied on conventional "luer lock" closures. These and similar closures have a finite 'dead' volume and this becomes proportionally larger as the volume of the bioreactor is reduced. This disadvantage can be circumvented by using ports of essentially no dead volume.

Luer lock closures can also lead to presence of air bubbles in the incubation compartment. Bioreactors are preferably kept free of air bubbles in the incubation compartment which otherwise have detrimental effects, breaking up the Spheriods. This air bubble problem is especially pronounced in a small volume bioreactor, where a single bubble can represent a relatively significant volume. Some solutions to the air bubble problem are known in the prior art. For example, WO 95/07344 provides a reservoir chamber for entrapping gas bubbles away from the incubation compartment. However, these solutions would be wholly unsuitable for a small volume bioreactor because of the volumes involved. A better solution is thus to provide a closure mechanism for access ports that excludes any possibility of introducing air bubbles into the incubation compartment.

Conventional "luer lock" and similar closures also increase fluid turbulence because they do not have a smooth inner surface and this can lead to increased shear forces which will have a detrimental effect on the Spheriods. Microgravity bioreactors require continuous rotation of the incubation compartment to maintain microgravity conditions for differentiated or differentiating cells and other tissues. If the incubation compartment inner surface is not suitably adapted, it may give rise to turbulence. Such turbulence may lead to tearing or "shearing" of Spheriods. Accordingly, it is advantageous to provide microgravity bioreactors with an access port closure mechanism that avoids turbulence. WO 95/07344, U.S. Pat. No. 5,153,131, U.S. Pat. No. 5,437,998, U.S. Pat. No. 5,665,594, U.S. Pat. No. 5,989,913, and U.S. Pat. No. 6,642,019 each disclose improvements of microgravity bioreactors. US 2005/0084965 discloses use of a conventional, commercially available microgravity bioreactor for incubating hepatocyte spheroids. However none of these patents or published applications addresses the problem of dehydration or discloses a microgravity bioreactor having a small incubation compartment volume or having a zero volume access port closure.

Prior art bioreactors of all volumes suffer yet another major problem, namely the difficulty of accessing the incubation chamber/cavity with instruments having dimensions exceeding e.g. a hypodermic syringe or pincers. Thus it is difficult to remove from the bioreactor individual or small amounts of Spheriods without risk of damage (e.g. by shear forces in using a syringe).

U.S. Pat. No. 5,576,211 and U.S. Pat. No. 5,153,131 describe cylindrical bioreactors being rotatable around a central axis, the bioreactors comprising a cell culture chamber and a supply chamber separated by a membrane. U.S. Pat. No. 5,153,131 does not disclose a removable lid, but instead the flange 22 not only constitute the end of the incubator but also the sidewall. Moreover, this flange is by far easy to remove and upon removal it disintegrates from the membrane. U.S. Pat. No. 5,576,211 is not a microgravity bioreactor (60 ml incubation volume), but only a roller-bottle system, and hence it will be difficult to access the entire culture chamber, when removing the screw-on ring. Moreover, even when the screw-on ring has been removed there is still a silicone membrane to cope with. Hence the bioreactor system of U.S. Pat. No. 5,576,211 does not provide easy access to the incubation cavity. In FIG. 9 in U.S. Pat. No. 5,576,211, there does not appear to be anything to hold the membrane support grid 82 in medium container 55. Likewise there is nothing to hold the dialysis membrane 64 against 82. Therefore, the user would have to empty or drain 55 before one can open into the cell culture chamber (between the dialysis membrane 64 and a gas exchange membrane in 72). Otherwise the dialysis membrane might fall out and spill the media.

Since microgravity is used to induce the cells to exhibit differentiated phenotypes, the cessation of rotation results in the Spheriods settling usually to the bottom of the incubation chamber. This can induce Spheriods to stick together or to the walls of the incubation chamber and start to lose the desirable phenotype. Thus if it is necessary to remove Spheriods from the incubation chamber, it must be possible to open the incubation chamber, remove one or more pieces of Spheriods and close the incubation chamber quite quickly (e.g. within a few minutes).

Accordingly, it is advantageous to provide an improved microgravity bioreactor that addresses these problems.

SUMMARY OF THE INVENTION

The present invention relates to a bioreactor (10) which is provided with a lid (13) that facilitates access to the incubation cavity. Specifically the end wall of the incubation cavity is constituted by the lid (13) so that removal of the lid renders the incubation cavity fully accessible.

This and several other objectives are obtained in a first aspect of the invention by providing a bioreactor adapted for rotation, the reactor comprising:
  an incubation cavity (15), the incubation cavity providing, in conjunction with, a semipermeable membrane (11) in the first end of the wall, and a sealable lid (13) which forms the second end of the wall and an essentially cylindrical wall, and provides a substantially closed confinement, said semipermeable membrane (11) being permeable to molecules up to a predetermined molecular weight or size, allowing a gas exchange in the incubation chamber and retention of cells and cellular aggregates in the incubation cavity, a reservoir chamber, said reservoir chamber providing a volume of water (or other dilute aqueous solutions) for the maintenance of very high humidity levels close to the semipermeable membrane 11, equilibrium chamber providing a conduit from the semipermeable membrane (11) to the reservoir chamber and a narrow connection to the external air surrounding the bioreactor (19), wherein said lid (13) is removably attached to the second end of the wall so as to provide access to the entire incubation cavity.

Optionally the lid (13) may have one or more ports at different locations.

In a second aspect, embodiments of the invention provide a bioreactor adapted for rotation, the bioreactor comprising an incubation cavity, the incubation cavity providing, in conjunction with an essentially cylindrical wall, a semipermeable membrane (11) in the first end of the wall, and a sealable lid (13) in the second end of the wall, a substantially closed confinement, wherein said lid (13) is removably attached to the second end of the wall so as to provide access to the entire incubation cavity, a reservoir chamber (18) comprising an aqueous liquid, the chamber comprising a humidifier (17) made of a suitable material to enhance high evaporation and equilibrium chamber (16) providing a conduit from the semipermeable membrane (12) to the humidifier (17) and a narrow connection to the external air surrounding the bioreactor (19), wherein the semipermeable membrane (12) is substantially impermeable to water and substantially permeable to oxygen and carbon dioxide so as to facilitate:

a) aeration of the incubation cavity through the semipermeable membrane (12) and b) substantial retainment of water in the incubation chamber.

In a preferred embodiment the reservoir has a port by which its contents can be replenished (21). Usually a water or aqueous solution will be used, but this solution may contain additives for special purposes (e.g. antibiotics and antimycotics for protection of the incubation chamber and conduit from infection).

In a preferred embodiment of the present invention the lid (13) is attached to the second end of the wall in a easily detachable manner (22). In this respect the incubation cavity may be lockable by virtue of a reversible snap-locking mechanism. In this way it is possible to open the incubation cavity, withdraw a portion of the Spheriods being cultivated, and close the incubation chamber in less than 10 minutes.

For the embodiments of the first and second aspect of the present invention is preferred that one or more of the following characteristics is/are satisfied:

the incubation cavity and the walls have a substantially cylindrical shape;

the bioreactor is adapted for rotation around a horizontal, rotational axis by associated rotation means, said rotational axis being substantially coincident with a central axis through the incubation cavity;

the lid (13) has at least one sealing port accessible with a tube for introducing or removing biological material to/from the incubation cavity;

removal of a portion of the Spheriods from the incubation cavity does not adversely affect the growth or physiological function of the Spheriods remaining in the incubation cavity;

it is possible to cultivate cells in the incubation cavity for about a week, more preferably several weeks or most preferably longer than a month (where the growth medium is changed appropriately);

the semipermeable membrane is permeable to small molecules, but can prevent bacteria, *mycoplasma* or other living organisms to get through; and the incubation cavity has an internal fluid volume selected from the group consisting of: about 25 µl to about 1000 ml, about 50 µl to about 500 ml, about 100 µl to about 200 ml, and about 200 µl to about 100 ml.

BRIEF DESCRIPTION OF THE DRAWING

Some embodiments of the present invention are illustrated by the accompanying Figures, where.

DETAILED DESCRIPTION OF THE INVENTION

Definitions

Figure 1:
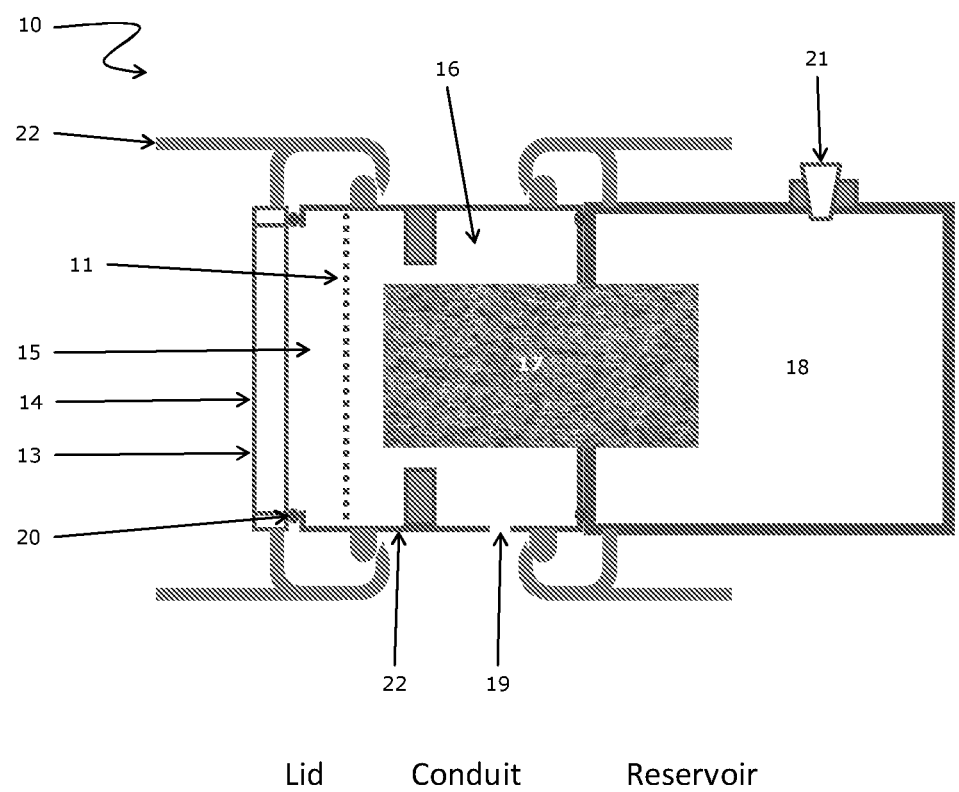
FIG. 1 is a schematic cross-sectional drawing of a bioreactor according to the first aspect of the invention.

As used herein, the following terms have the following meanings:

The terms "semipermeable membrane" refer to a membrane that can be penetrated by some, but not all, chemical or biological substances.

The term "incubation cavity" refers to that portion of a bioreactor in which cell cultures, tissue biopsies, cell clusters, spheroids, tissue-like structures, "Spheriods" or similar samples are grown, differentiated, incubated, or otherwise cultured. The term "incubation cavity" is used interchangeably with "incubation chamber" and "incubation compartment."

The term "substantially impermeable to water" is used to describe characteristics of membranes of the present invention and refers to a membrane that exhibits a high degree of repulsion of water and water-like molecules in gas and/or liquid phase.

The term "almost completely impermeable to water" is used to describe characteristics of membranes of the present invention and refers to a membrane across which the water flow rate at 1 bar is not greater than 0.1 mL/min/cm$^2$.

The term "substantially permeable to oxygen and carbon dioxide" is used to describe characteristics of membranes of the present invention and refers to a membrane across which air will readily pass.

The term "relative retainment" is used to describe conditions arising from operation of a bioreactor of the invention with an aqueous solution or suspension in the incubation cavity and refers to the relative amount of residual substance initially present. For example, the relative retainment of water in the incubation cavity (with a flexible membrane) may be calculated as the volume of the cavity after operating the bioreactor divided by the volume of the cavity at the beginning of operating the bioreactor.

The term "toxic" has the usual meaning known in the art. A "toxic" substance is a substance that in the amount present in the chemical compositions as defined above can impair the functioning of, or cause structural damage to a cell, tissue or organism.

The term "predetermined toxicity" relates to both toxic and non-toxic substances. As Paracelsus stated in the 16$^{th}$ century, "All things are poison and nothing is without poison, only the dose permits something not to be poisonous". The toxicity type of a substance may e.g. be determined according to the toxicity typing scheme of the Food and Drug Administration (FDA) of the United States of America. According to this scheme, the predetermined toxicity of a substance may belong to toxicity type A, B, etc. or may be non-toxic.

The term "cell cultures" refers to any kind of cells, tissue biopsies, cell clusters, tissue-like structures, "Spheriods" or similar samples obtained or initially cultured by any method known in the art.

The term "cells" refers to primary, immortal or stem cells from any type of living organism, whether archaea, prokaryote or eukaryote, and also includes viruses or other entities that need living cells to replicate.

The term "microgravity bioreactor" refers to a bioreactor adapted for rotation.

The term "incubating under microgravity conditions" refers to growth of cell cultures in a bioreactor adapted for rotation while rotating said bioreactor about a substantially horizontal central axis at a rate that suspends one or more cell cultures in a liquid culture medium and continuing such rotation for a time period that permits growth of said one or more cell cultures.

The term "means of relative retainment of water" is used to describe features of a bioreactor and refers to any means other than perfusion that is used in combination with a membrane that substantially confines the incubation chamber to achieve relative retainment of water in the incubation chamber or, in the alternative, to any single membrane that substantially confines the incubation chamber across which membrane the water flow rate at 1 bar is not greater than 0.1 mL/min/cm$^2$.

Preferred Embodiments

In preferred embodiments, the semipermeable membranes utilised in the present invention allow passage of molecules up to a certain molecular weight or size. Semipermeable membranes with a well-defined pore size are known to the person skilled in the art and are commercially available. In preferred embodiments of the invention, semipermeable membranes may be permeable to molecules up to a predetermined molecular weight, such as 50 kDa, 100 kDa, 150 kDa, 200 kDa or 250 kDa. Alternatively, the permeability of semipermeable membranes may be determined by the pore sizes therein. The pore size of semipermeable membranes may be less than or equal to 0.5 µm, such as less than or equal to 0.3 µm, preferably less than or equal to 0.2 µm, even more preferably less than or equal to 0.1 µm, and most preferably less than or equal to 0.05 µm. A membrane with pore sizes of 0.22 µm is generally considered sufficient to prevent bacteria and *mycoplasma* from crossing the membrane. A wide variety of membranes can be used. These could be made of materials selected from (but not limited to) the group consisting of polytetrafluroethylene (PTFE), Polyvinylidene fluoride (PVDF), silicon rubber, foam plastics, radiation treated plastic, and similar materials. In one preferred embodiment, a TE 35 filter from Whatman or a Zefluor filter (cat. no. 66142 from Pall Life Sciences can be used.

In preferred embodiments of the invention, the water flow rate at 1 bar across membranes that are "substantially impermeable to water" and "substantially permeable to oxygen and carbon dioxide" is not greater than 50 ml/min/cm$^2$, preferably not greater than 40 ml/min/cm$^2$, more preferably not greater than 30 ml/min/cm$^2$, even more preferably not greater than 20 ml/min/cm$^2$, most preferably not greater than 10 ml/min/cm$^2$. It will be readily understood by those skilled in the art that water permeability can be expressed in other units, which can be converted into ml/min/cm$^2$.

In preferred embodiments of the invention, the air flow rate at 3 mbar across membranes that are "substantially impermeable to water" and "substantially permeable to oxygen and carbon dioxide" is at least 5 ml/min/cm$^2$, preferably at least 10 ml/min/cm$^2$, more preferably at least 15 ml/min/cm$^2$, even more preferably at least 20 ml/min/cm$^2$, most preferably at least 25 ml/min/cm$^2$. It will be readily understood by those skilled in the art air flow can be expressed in other units, which can be converted into ml/min/cm$^2$.

Membranes comprised of a wide variety of materials can be used, that are "substantially impermeable to water" and "substantially permeable to oxygen and carbon dioxide," including but not limited to membranes well known in the art comprised of polytetrafluoroethylene (PTFE), Polyvinylidene fluoride (PVDF), silicon rubber, foam plastics, radiation treated plastic or similar materials. One example of a suitable membrane is commercially available from Whatman under the trade mark "TE 35®," a PTFE membrane with polyester support having characteristics (quoted by the manufacturer): pore size 0.2 µM, thickness 190 µM, water flow rate at 0.9 bar of 20 ml/min/cm$^2$ when measured with ethanol, air flow rate 15 ml/min/cm$^2$ at 3 mbar and bubble point 1.4 bar. Another example of a suitable membrane is commercially available from Millipore under the trade mark "SureVent®," a PVDF membrane having characteristics (quoted by the manufacturer): pore size 0.22 µM, thickness 100-150 µM, water breakthrough 45 mbar, air flow rate >1 slpm/cm$^2$ at 10 psi. In some embodiments, the membranes can be Millipore 0.22 µm "Durapel" membranes or Whatman TE 35 and TE36 membranes.

In preferred embodiments of the invention, the water flow rate at 1 bar across membranes that are "almost completely impermeable to water" while "substantially permeable to oxygen and carbon dioxide" is not greater than 0.1 ml/min/cm$^2$, even more preferably not greater than 0.05 mL/min/cm$^2$, still more preferably not greater than 0.04 ml/min/cm$^2$, even more preferably not greater than 0.03 ml/min/cm$^2$, still more preferably not greater than 0.02 ml/min/cm$^2$, most preferably not greater than 0.01 ml/min/cm$^2$. It will be readily understood by those skilled in the art that water permeability can be expressed in other units, which can be converted into ml/min/cm$^2$.

In preferred embodiments of the invention, the air flow rate at 3 mbar across membranes that are "almost completely impermeable to water" while "substantially permeable to oxygen and carbon dioxide" is at least 5 ml/min/cm$^2$, preferably at least 10 ml/min/cm$^2$, more preferably at least 15 ml/min/cm$^2$, even more preferably at least 20 ml/min/cm$^2$, most preferably at least 25 ml/min/cm$^2$.

Membranes comprised of a wide variety of materials can be used, that are "almost completely impermeable to water" while "substantially permeable to oxygen and carbon dioxide" including but not limited to membranes initially prepared for ultrafiltration purposes that have very low water permeabilities at atmospheric pressures, for example, due to low porosity and high hydrophobicity. Such membranes include ultrafiltration membranes commercially available from Amicon under the trademark "YM10" and from Pall Corp. under the trademark "Omega 1 K.®". Other suitable membranes include thermoplastic ultrafiltration membranes prepared by thermally induced phase inversion process of semi-crystalline materials such as poly(ether ether ketone) (PEEK) and poly(phenylene sulfide) (PPS), as described by [Micro- and ultrafiltration film membranes from poly(ether ether ketone) (PEEK). Sonnenschein M, Journal of Applied Polymer Science 1999 74:1146]. Immobilized, stable supported liquid membranes (SLM) can also be used comprising a suitable oligomeric or polymeric liquid membrane material immobilized within a solid, microporous, hydrophobic support, such as the system disclosed in U.S. Pat. No. 5,507,949.

In a preferred embodiment of the invention, cells that can be applied in the context of the present invention are selected from the group consisting of hepatocytes, adipocytes, kidney cells, muscle cells, or similar cells, liver tissue, fat tissue (brown or white), liver biopsies, kidney biopsies, muscle biopsies, ovarian follicles, islets of Langerhans, and all cancer cells derived therefrom.

In a particularly preferred embodiment of the invention, cells that can be applied in the context of the present invention are hepatocytes, in particular human hepatocytes.

FIG. 1 is a schematic cross-sectional drawing of a bioreactor 10 according to the first aspect of the invention. The bioreactor 10 has a high degree of rotational symmetry around a horizontal axis as viewed in FIG. 1. The reactor comprises an incubation cavity 15 for incubation of cells, tissues etc. The incubation cavity provides, in conjunction with an essentially cylindrical wall, a semipermeable membrane (11) in the first end of the wall, and a sealable lid (13) in the second end of the wall, a substantially closed confinement (using optionally an O-ring (22). The incubation cavity (15) provides, in conjunction with a semipermeable membrane (12) (also known as a sterile filter) (11), a substantially closed confinement for incubation of cells etc. In order to provide nutrients and/or fresh fluid culture medium, the semipermeable membrane 11 is permeable to molecules up to a predetermined molecular weight, such as 50 kDa, 100 kDa, 150 kDa, 200 kDa or 250 kDa. Standard dialysis membranes can fulfil these requirements. Alternatively, the permeability of the semipermeable membrane 11 is determined by the pore sizes therein. The pore size of the semipermeable membrane 11 may be less than or equal to 0.5 μm, such as less than or equal to 0.3 μm, preferably less than or equal to 0.2 μm, even more preferably less than or equal to 0.1 μm, and most preferably less than or equal to 0.05 μm. Sizes less than or equal to 0.2 μm are preferable because of the need to prevent infections (e.g. bacteria, *mycoplasma* or yeasts) entering through the membrane. In this preferred embodiment the main purpose of the semipermeable membrane is to allow exchange of nutrients and waste products while excluding cells and bacteria from entering (or leaving) the incubation cavity. Thus a wide variety of membranes could be used for 11. These could be made of polytetrafluroethylene (PTFE), Polyvinylidene fluoride (PVDF), silicon rubber, foam plastics, radiation treated plastic or similar materials. Thereby an inflow of nutrients and fluid culture medium into the incubation chamber is provided while at the same time providing retainment of cells and cellular aggregates and their protection from external infection in the incubation cavity 15. The incubation cavity 15 has an internal fluid volume of about 25 μl to about 1,000 ml. Preferably, the fluid volume of the incubation cavity 15 is about 50 μl to about 500 ml, more preferably about 0.1 to about 200 ml. Small sizes significantly reduces the cost of use and the amount of materials (both organic and inorganic) necessary for successful operation. Small size will facilitate close-up monitoring of the cells (e.g. by remote camera or microscope), and automated processing.

The larger sizes will allow for the preparation of larger amounts of spheriods which have uniform characteristics which may be used for regenerative medicine, the preparation of large amounts of metabolites (e.g. from drugs or other compounds) or for the subdivision into small aliquots for further experimentation.

In the front of the bioreactor 10, a transparent section 14 is located so that the cultivation of cells etc. may be monitored and assessed visually, either manually or automatically with e.g. a camera, from outside of the bioreactor 10. The transparent section 14 could be made of glass, plastic or any other suitable materials being both transparent and biologically and chemically inert with respect to the cell cultivation process. Preferred materials would include (but not be limited to) various types of glass, polystyrene, polycarbonate, polypropylene, polyethylene and Polymethyl methacrylate (PMMA). Suitable variants of polymethyl methacrylate (PMMA) are available commercially including products marketed under the trademarks/trade names Perspex®, Plexiglas®, Lucite®, Acrylite®, Rhoplex®, and Oroglas®. Any embodiment of the bioreactor could be made in whole or in part from such transparent materials.

The incubation cavity 15 preferably has a substantially cylindrical shape but other shapes are also possible, e.g. elliptical shapes, spherical shapes etc. Preferably, the bioreactor 10 is adapted for rotation around a horizontal, rotational axis by associated rotation means (not shown) to facilitate growth of the cells in the cavity 15. The rate of rotation is adjusted to maintain the cells or Spheriods in suspension and this rate has to be varied as the size of the Spheriods increases. The person skilled in the art will know how to adjust the rotation speed in order to maintain the cells or Spheriods in suspension.

Figure 2:
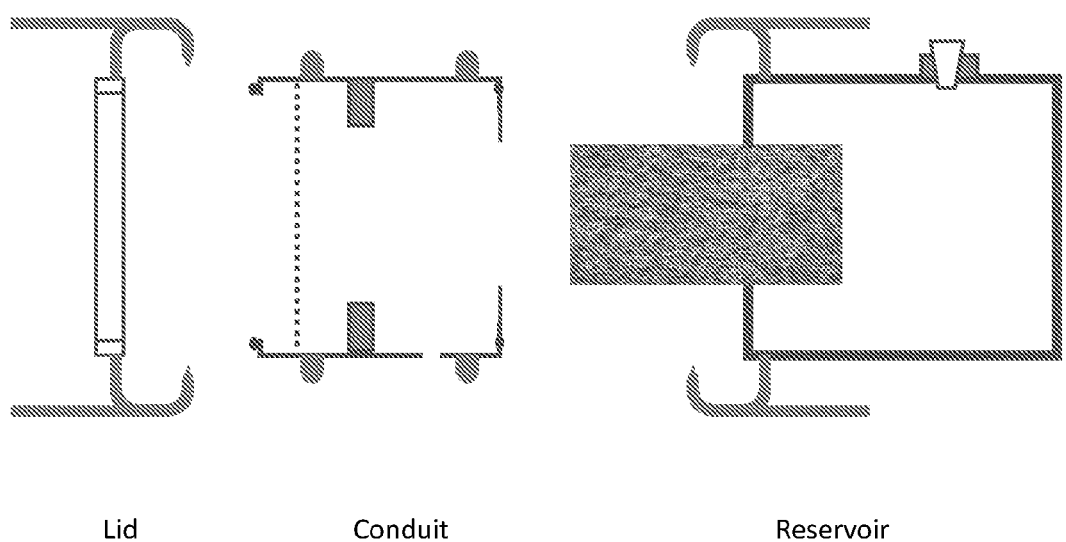
FIG. 2 is an exploded version of FIG. 1 where the three main components are separated.

FIG. 2 is an exploded version of FIG. 1 where the three main components are separated.

The invention claimed is:

1. A bioreactor adapted for rotation, the bioreactor comprising:
    an incubation chamber including an incubation cavity defined by a first cylindrical wall section extending from a first end of the incubation chamber to a second end of the incubation chamber, and a central axis extending from the first end to the second end, wherein the first end of the incubation chamber comprises a semipermeable membrane, permeable to gases and impermeable to cells and cellular aggregates, and wherein the second end of the incubation chamber is an open end;
    a lid removably attached to the first cylindrical wall section at the open end of the incubation chamber, the lid comprising a transparent section for visually monitoring the incubation cavity when the lid is coupled with the first wall section;
    a reservoir for housing aqueous media, wherein the reservoir comprises a second wall section extending from a first end of the reservoir to a second end of the reservoir; and
    an equilibrium chamber positioned between the incubation chamber and the reservoir and comprising a third wall section extending between the first end of the incubation chamber and the first end of the reservoir, said equilibrium chamber comprising a volume for an exchange of gasses; and a humidifier having a first portion arranged in the reservoir, a second portion arranged in the equilibrium chamber and extending from the reservoir to the equilibrium chamber wherein the humidifier is configured to facilitate evaporation of the aqueous media from the reservoir into the equilibrium chamber, wherein the bioreactor is configured to be rotated about a central rotational axis that coincides with the central axis of the incubation cavity.

2. The bioreactor according to claim 1, wherein the lid comprises a locking mechanism for coupling the lid with the first wall section.

3. A The bioreactor according to claim 1, wherein the bioreactor is configured for rotation around the rotational axis by associated rotation means.

4. The bioreactor according to claim 1, wherein the lid comprises a sealable port accessible with a tube for introducing or removing biological material to/from the incubation cavity.

5. The bioreactor according to claim 1, wherein the semipermeable membrane is impermeable to bacteria, *mycoplasma* and other living organisms.

6. The bioreactor of claim 2, wherein the locking mechanism comprises a snap closure.

7. The bioreactor of claim 1, wherein the reservoir comprises a port for refilling the reservoir.

8. The bioreactor of claim 1, wherein the lid is constructed to provide direct access to the entire volume of the incubation cavity when the lid is removed.

9. The bioreactor of claim 1, wherein the bioreactor is constructed to be operated as a microgravity incubator.

10. The bioreactor of claim 1, wherein the rotational axis is a horizontal axis.

* * * * *